United States Patent [19]

Pugach

[11] 4,284,585
[45] Aug. 18, 1981

[54] PROCESS FOR THE PREPARATION OF ACETIC ANHYDRIDE

[75] Inventor: Joseph Pugach, Ho-Ho-Kus, N.J.

[73] Assignee: Halcon Research and Development Corp., New York, N.Y.

[21] Appl. No.: 106,627

[22] Filed: Dec. 26, 1979

[51] Int. Cl.$^3$ .............................................. C07C 51/56
[52] U.S. Cl. ..................................... 260/549; 260/546
[58] Field of Search .............................. 260/546, 549

[56] References Cited

U.S. PATENT DOCUMENTS

| | | | |
|---|---|---|---|
| 4,102,920 | 7/1978 | Bartish | 560/232 |
| 4,115,444 | 9/1978 | Rizkalla | 260/549 |

Primary Examiner—Paul J. Killos
Attorney, Agent, or Firm—William C. Long; David Dick; Riggs T. Stewart

[57] ABSTRACT

Acetic anhydride is prepared from methyl acetate and/or dimethyl ether in carbonylation processes comprising the use of a halide, carbon monoxide and a Group VIII noble metal in the presence of promoters comprising metallic zirconium and an organo-phosphorus compound or an organo-nitrogen compound wherein the phosphorus and nitrogen are trivalent, or an arsine of the formula:

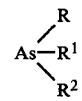

wherein R and $R^1$ are monocyclic aryl groups or alkyl groups and $R^2$ is the radical

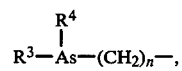

a monocyclic aryl group or an alkyl group, and wherein $R^3$ and $R^4$ are each a monocyclic aryl group or an alkyl group, n being zero or a digit from 1-20.

7 Claims, No Drawings

PROCESS FOR THE PREPARATION OF ACETIC ANHYDRIDE

This invention relates to the preparation of acetic anhydride by carbonylation.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has wellknown drawbacks and disadvantages and the search for an improved process for the production of acetic anhydride has been a continuing one. Proposals for producing anhydrides by the action of carbon monoxide upon various reactants (carbonylation) have been described, for example, in Reppe et al. U.S. Pat. Nos. 2,729,561, 2,730,546 and 2,789,137. However, such prior proposals involving carbonylation reactions have required the use of very high pressure. Carbonylation at lower pressures has been proposed but as a route to the preparation of acetic acid. French Pat. No. 1,573,130, for example, describes the carbonylation of methanol and mixtures of methanol with methyl acetate in the presence of compounds of iridium, platinum, palladium, osmium and ruthenium and in the presence of bromine or iodine under more moderate pressures than those contemplated by Reppe et al. Similarly, South African Pat. No. 68/2174 produces acetic acid from the same reactants using a rhodium component with bromine or iodine components. Schultz (U.S. Pat. Nos. 3,689,533 and 3,717,670) has disclosed a vapor-phase process for acetic acid production employing various catalysts comprising a rhodium component dispersed on a carrier.

More recently, Belgian Pat. No. 819,455 shows the carbonylation of certain esters and/or ethers to produce carboxylic acid anhydrides employing Group VIII noble metal catalysts in the presence of bromine or iodine moieties optionally in the presence of promoters comprising at least one metal which is an element having an atomic weight greater than 5 of Groups IA, IIA, IIIA, IVB and VIB, a non-noble metal of Group VIII or a metal of the lanthanide and actinide groups of the Periodic Table, and their compounds. U.S. Pat. No. 3,927,078 shows the preparation of acetic anhydride by the carbonylation of methyl acetate or dimethyl ether in the presence of a Group VIII noble metal compound and in the presence of an iodide or bromide promoter and is characterized by the inclusion of a proton donor in the reaction system. The optional use of Lewis acids is also disclosed. U.S. Pat. No. 4,046,807 of Sept. 6, 1977 also shows the carbonylation of methyl acetate to produce acetic anhydride using noble metal compound catalysts and iodides and shows the use of triphenylphosphine as a promoter alone or in combination with cobalt acetate. Belgian Pat. No. 839,321 shows a process for the preparation of ethylidene diacetate by the reaction of carbon monoxide and hydrogen upon methyl acetate or dimethyl ether using a Group VIII noble metal catalyst in the presence of an iodide or bromide and in the presence of a promoter which may be a phosphine, an arsine or a stibine. In some cases, acetic anhydride is produced as a by-product.

More recently, U.S. Pat. No. 4,115,444 dated Sept. 19, 1978 discloses an improved process for preparing carboxylic acid anhydrides, including acetic anhydride, wherein specified esters and/or ethers are carbonylated in the presence of Group VIII noble metals or their compounds in a system containing an iodide or a bromide and in the presence of a promoter of at least one metal of Groups IVB, VB and VIB or a non-noble metal of Group VIII, or their compounds, in combination with an organo-nitrogen compound or an organo-phosphorus compound wherein the nitrogen and phosphorus are trivalent.

It is an object of the present invention to provide a further improved process for the manufacture of acetic anhydride and, in particular, to provide an improvement in the process of U.S. Pat. No. 4,115,444.

In accordance with the invention, methyl acetate and/or dimethyl ether are carbonylated under substantially anhydrous conditions in the presence of a Group VIII noble metal catalyst, in the presence of a halide which is an iodide or a bromide and in the presence of promoters comprising zirconium in metallic or zero valent form in combination with an organo-phosphorus compound or an organo-nitrogen compound wherein the nitrogen and phosphorus are trivalent, or an arsine.

It has been discovered that this catalyst-multiple promoter system makes possible surprisingly increased reaction rates. The rate of reaction and the product concentration per unit of time realized from this catalyst-multiple promoter combination have been found to be unexpectedly exceptionally high.

The Group VIII noble metal catalyst, i.e., iridium, osmium, platinum, palladium, rhodium and ruthenium, can be employed in any convenient form, viz., in the zero valent state or in any higher valent form. For example, the catalyst to be added may be the metal itself in finely divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Similarly, complexes of the metals can be employed, for example the metal carbonyls, such as iridium carbonyls and rhodium carbonyls, e.g., hexarodium hexadecacarbonyl, or as other complexes such as the carbonyl halides, e.g., iridium tri-carbonyl chloride $[Ir(CO)_3Cl]_2$ or chlorodicarbonyl rhodium dimer, or the acetylacetonates, e.g., rhodium acetylacetonate $Rh(C_5H_7O_2)_3$. Included among the catalysts listed above are complexes of the Group VIII noble metal with organic promoter ligands derived from the organic promoters hereinabove described. It will be understood that the foregoing compounds and complexes are merely illustrative of suitable forms of the Group VIII noble metal catalyst and are not intended to be limiting.

As previously indicated, the zirconium is employed in metallic or zero valent form, zirconium in this form having been surprisingly found to exhibit activity not shared by zirconium compounds. Moreover, the zirconium metal requires the presence of acetic acid in order for its surprising and unexpected activity to be realized. Furthermore, it has been found that the zirconium is effective with an arsine or organo-phosphorus or nitrogen compounds as defined below but is inactive with stibines even though stibines are often grouped with arsines and organo-phosphorus compounds such as phosphines.

The arsines employed in accordance with this invention have the formula:

wherein R and $R^1$ are monocyclic aryl groups or alkyl groups and $R^2$ is the radical

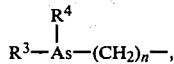

a monocyclic aryl group or an alkyl group, and wherein $R^3$ and $R^4$ are each a monocyclic aryl group or an alkyl group. It is preferred that at least one of R, $R^1$ and $R^2$ is a monocyclic aryl group, n being zero or a digit from 1–20. The alkyl groups in the foregoing formula are preferably lower alkyl groups of 1–8 carbon atoms, such as methyl, ethyl, propyl, butyl, hexyl and octyl, especially 1–4 carbon atoms, but may contain as many as 20 carbon atoms. Similarly, the aryl group is preferably phenyl but may be phenyl substituted with one or more alkyl groups containing one or more carbon atoms, e.g., up to 6 carbon atoms, such as methyl, ethyl, propyl, butyl, and hexyl. The phenyl groups can also be substituted with other non-reactive substituents such as halo, e.g., chloro, or cyano, and the like. Typical examples of the arsines used in the process of this invention include triphenylarsine, tri-p-tolylarsine, dimethylphenylarsine, methyldiphenylarsine, methylditolylarsine, dimethylchlorophenylarsine, dimethylcyanophenylarsine, bis-(diphenylarsino) methane, bis-(diphenylarsino) ethane, bis-(diphenylarsino) propane, bis-(diphenylarsino) butane, tetraphenyl bi-arsine, triethyl arsine, and the like. Most preferred are the alkyl diaryl arsines, especially methyldiphenylarsine.

The nitrogen and phosphorous promoters can, in a broad sense, be any organo-nitrogen or organo-phosphorus compound wherein the nitrogen and phosphorus are trivalent. Preferably, however, the organo-nitrogen co-promoter is an amine, especially a tertiary amine of the formula

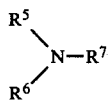

wherein $R^5$, $R^6$ and $R^7$ are the same or different and are alkyl, cycloalkyl, aryl or acyl groups which may be substituted by non-interfering groups, preferably having up to 20 carbon atoms, such as trimethylamine, triethylamine, triphenylamine, ethylenediamine, tetraacetic acid, and the like, or a heterocyclic amine such as pyridine, picoline, quinoline, methylquinoline, hydroxy quinoline, pyrrole, pyrrolidine, pyrrolidone, and the like, or an imidazole, such as imidazole, methyl imidazole and the like, or an imide of a carboxylic acid which may be monobasic or polybasic and which may be aliphatic or aromatic and preferably contain up to 20 carbon atoms, such as acetic acid, succinic acid, phthalic acid, pyromellitic acid, e.g., succinimide, phthalimide and pyromellitic diimide, or a nitrile or an amide which may be aliphatic or aromatic and preferably contains up to 20 carbon atoms, e.g., acetonitrile, N,N-dimethylacetamide, hexamethyl phosphoric triamide, and like imides nitriles, and amides, or an oxime such as cyclohexanone oxime, and the like. It will be understood, however, that higher molecular weight promoters, e.g., polymeric forms of the organo-nitrogen compounds, may be used such as polyvinylpyridine, polyvinyl pyrrolidone, and the like.

The organo-phosphorus co-promoter is preferably a phosphine of the formula:

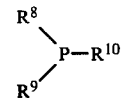

wherein $R^8$ and $R^9$ may be the same or different and are alkyl, cycloalkyl, aryl groups, amide groups or halogen atoms and $R^{10}$ is an alkyl, cycloalkyl, aryl, amide group, a halogen atom or the radical

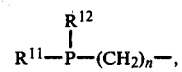

$R^{11}$ and $R^{12}$ each being an aryl group or an alkyl group and n being zero or a digit from 1–20. Preferably, the groups contain up to 1 to 20 carbon atoms in the case of alkyl and cycloalkyl groups and 6 to 18 carbon atoms in the case of aryl groups. Typical phosphines include trimethylphosphine, tripropylphosphine, tricyohexylphosphine and triphenylphosphine.

Although it is preferred that the organic promoters be added separately to the catalyst system, it is possible to add them as complexes with the Group VIII noble metal such as the trichloro trispyridine rhodium, tris(-triphenyl phosphine) rhodium, chlorotris(triphenyl phosphine) rhodium, and chlorocarbonyl bis(triphenyl phosphine) rhodium previously mentioned. Both free organic promoters and complexed promoters can also be used. Indeed, when a complex of the organic promoter and the Group VIII noble metal is used, it is desirable to add free organic promoter as well.

In carrying out the process of the present invention, carbon monoxide is reacted with methyl acetate or dimethyl ether to produce acetic anhydride, the carbonylation taking place in the presence of an iodide or bromide, e.g., a hydrocarbyl halide, especially a lower alkyl halide, which is an iodide or bromide, such as methyl iodide. Thus, acetic anhydride can be effectively prepared in a representative case by subjecting methyl acetate or dimethyl ether to carbonylation in the presence of methyl iodide. In all cases, the carbonylation is carried out under substantially anhydrous conditions in the presence of the catalyst-multiple promoter system described above. As indicated, an ester-ether mixture can be carbonylated if desired.

It will be understood that the hydrocarbyl halide may be formed in situ and the halide may thus be supplied to the system not only as the hydrocarbyl halide but the halogen moiety may also be supplied as another organic halide or as the hydrohalide or other inorganic halide, e.g., a salt, such as the alkali metal or other metal salts, or even as elemental iodine or bromide. Following the reaction the organic components of the reaction mixture are readily separated from one another, as by fractional distillation.

The above-described reactions can be expressed as follows:

$$CO + CH_3COOCH_3 \rightarrow (CH_3CO)_2O \quad (1)$$

$$2CO + CH_3OCH_3 \rightarrow (CH_3CO)_2O \quad (2)$$

The more volatile alkyl halide and any unreacted ether or ester which are present in the final reaction mixture can be readily removed, as by distillation, for recycling, and the net yield of product is substantially exclusively the desired carboxylic anhydride. In the case of liquid-phase reaction, which is preferred, the organic compounds are easily separated from the metal-containing components, as by distillation. The reaction is suitably carried out in a reaction zone to which the carbon monoxide, the ester or ether, the halide and the noble metal catalyst and the promoters are fed. No water is produced in the above-described reactions and anhydrous or substantially anhydrous conditions are employed.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction depends largely upon the temperature employed. The reaction is carried out under superatmospheric pressure but excessively high pressures, which require special high-pressure equipment, are not necessary. In general, the reaction is effectively carried out by employing a carbon monoxide partial pressure which is preferably 15 to 1,000 p.s.i., and most preferably 30 to 700 p.s.i., although carbon monoxide partial pressures of 1 to 10,000 p.s.i can also be employed. By maintaining the partial pressure of carbon monoxide at the values specified, adequate amounts of this reactant are always present. The total pressure is preferably that required to maintain the liquid phase and in this case the reaction can be advantageously carried out in an autoclave or similar apparatus. Preferably, the reaction product is introduced into a distillation zone, which may be a fractional distillation column, or a series of columns, effective to separate the hydrocarbyl halide and the ester or ether, free organic promoter and the product anhydride. The boiling points of these several compounds are sufficiently far apart that their separation by conventional distillation presents no particular problem. Likewise, the higher boiling organic components can be readily distilled away from the noble metal catalyst, the zirconium promoter, and any organic promoter which may be in the form of a relatively non-volatile complex. The hydrocarbyl halide and the noble metal catalyst and the promoters, can then be combined with fresh amounts of ester or ether and carbon monoxide and reacted to produce additional quantities of anhydride.

The ratio of ester or ether to the halide in the reaction system can vary over a wide range. Typically, there are used 0.1 to 1,000 mols of the ester or ether per mol of halide, preferably 1 to 30 mols per mol.

The process is, as mentioned, carried out in the presence of acetic acid and, indeed, effective results require the presence of acetic acid in amounts of 1 to 75 wt. percent, preferably 10 to 30 wt. percent, of the total reaction mixture. Other organic solvents or diluents may be used in addition to acetic acid, if desired, particularly when the reactant has a relatively low boiling point, as in the case of dimethyl ether. The presence of a higher boiling solvent or diluent, which may be the product anhydride itself, e.g., acetic anhydride in the case of dimethyl ether, or which may be the corresponding ester, e.g., methyl acetate, again in the case of methyl ether, will make it possible to employ more moderate total pressure. Alternatively, the additional solvent or diluent may be any organic solvent which is inert in the environment of the process such as hydrocarbons, e.g., octane, benzene and toluene. A solvent or diluent is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like other reactants should, however, be essentially dry, i.e., the CO and the other reactants should be reasonably free from water. The presence of minor amounts of water such as may be found in the commercial forms of the reactants is, however, entirely acceptable. Hydrogen which may be present in very small amounts as an impurity is not objectionable and even may tend to stabilize the catalyst.

The metals employed may contain impurities normally associated with the commercially available metal or metal compounds, and need not be purified any further. Thus, the commercially available metal or metal compound is suitably employed in the case of the Group VIII noble metal catalyst and the commercially available zirconium metal and may be employed as the metal promoter.

Although it is preferred that the arsine, phosphorus or nitrogen promoters be added separately to the catalyst system, it is possible to add them as complexes with the Group VIII noble metal such as chlorotris-(triphenylarsine) rhodium, chlorocarbonyl (triphenylarsine) rhodium, hydridocarbonyltris-(triphenylarsine) rhodium, the corresponding methyldiphenylarsine compounds, trichlorocarbonyl-bis-(triphenylarsine) rhodium, and trichlorocarbonyl-bis-(methyldiphenylarsine) rhodium, trichlorocarbonyl-bis-(triethylarsine) rhodium, and the corresponding phosphorus and nitrogen compound complexes, and the like. Both free organic promoters and complexed promoters can also be used. Indeed, when a complex of the organic promoter and the Group VIII noble metal is used, free organic promoter may be added as well, if desired.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate. However, essentially any amount of catalyst will facilitate the basic reaction and can be considered a catalytically-effective quantity. Typically, however, the catalyst is employed in the amount of 1 mol per 10 to 100,000 mols of ester or ether, preferably 1 mol per 100 to 10,000 mols of ester or ether, and most preferably 1 mol per 500 to 2,000 mols of ester or ether.

The quantity of zirconium promoter can vary widely. Typically, it is one mol per 10,000 mols of ester or ether, preferably it is used in the amount of 1 mol per 20 to 2,000 mols, most preferably 1 mol per 50 to 500 mols of ester or ether. The quantity of organic promoter can also vary widely but typically it is used in the amounts of 1 mol per 1 to 10,000 mols of ester or ether, preferably 1 mol per 10 to 1,000, most preferably 15 to 200 mols of ester or ether.

In the working up of the reaction mixtures, e.g., by distillation, as discussed above, the zirconium promoter generally remains with the Group VIII noble metal catalyst, i.e., as one of the least volatile components, and is suitably recycled or otherwise handled along with the catalyst. The organic promoter can also be recovered and recycled.

It will be apparent that the above-described reactions lend themselves readily to continuous operation in which the reactants and catalyst, preferably in combination with the promoter combination, are continuously supplied to the appropriate reaction zone and the reaction mixture continuously distilled to separate the volatile organic constituents and to provide a net product consisting essentially of the acetic anhydride, with the other organic components being recycled and, in the case of liquid-phase reaction, a residual Group VIII noble metal-containing (and promoter-containing) fraction also being recycled. In the case of such continuous operation, it will be apparent that the halogen moiety remains in the system at all times subject only to occasional handling losses or purges. The small amount of halogen makeup which may be needed from time to time is preferably effected by supplying the halogen in the form of the hydrocarbyl halide but, as pointed out above, the halogen moiety may also be supplied as another organic halide or as the hydrogen halide or other inorganic halide, e.g., a salt, such as the alkali metal or other metal salts, or as elemental iodine or bromine.

The following examples will serve to provide a fuller understanding of the invention, but it is to be understood that they are given for illustrative purposes only, and are not to be construed as limitative of the invention. In the examples, all percentages are by weight, unless otherwise indicated.

In the examples, the various reactants and catalyst components are charged to the reaction vessel which is then closed and brought to the reaction temperature indicated. The initial carbon monoxide partial pressure specified is the calculated value at reaction temperature at the beginning of the reaction, i.e., at zero conversion. The total pressure is maintained by introducing additional carbon monoxide as the reaction proceeds.

EXAMPLE I

A mixture of 80 wt.% methyl acetate and 20 wt.% of acetic acid containing 0.01 mol per liter of rhodium trichloride hydrate, 0.6 mol per liter of methyl iodide, 0.04 mol per liter of zirconium metal in the form of powder and 0.16 mol per liter of triphenylarsine was heated at 160° C. in a stirred Hastelloy pressure vessel, under an atmosphere of carbon monoxide (continuous total pressure 700 psig; initial partial pressure of carbon monoxide 400 psig). G.C. (gas chromatography) analysis of the reaction mixture after a 6-hour reaction time showed it to contain 54.9% acetic anhydride, the balance being unreacted methyl acetate and the catalyst and promoter components.

EXAMPLE II

Example I was repeated except that 0.16 mol per liter of tri-n-butylphosphine was used instead of the arsine. After 6 hours of reaction, G.C. analysis showed the reaction mixture to contain 39.2% acetic anhydride.

EXAMPLE III

Example I was again repeated except that 0.16 mol per liter of tri-phenylphosphine was used instead of the arsine. After 6 hours of reaction, G.C. analysis showed the reaction mixture to contain 51.1% acetic anhydride.

EXAMPLE IV

Example I was repeated except that there were used 0.16 mol per liter of pyridine instead of the arsine. G.C. analysis of the reaction mixture showed it to contain 55.1% acetic anhydride.

COMPARATIVE EXAMPLE A

Example I was repeated except that acetic acid was omitted from the reaction mixture. G.C. (gas chromatography) analysis of the reaction mixture after a 6-hour reaction time showed it to contain 22.6% acetic anhydride.

COMPARATIVE EXAMPLE B

Example I was again repeated but using 0.04 mol per liter of zirconium in the form of biscyclopentadienyl zirconium chlorohydride. G.C. analysis of the reaction mixture showed it to contain 20.5% acetic anhydride.

COMPARATIVE EXAMPLE C

In this case, Example I was again repeated except that 0.04 mol per liter of zirconium was supplied in the form of zirconium oxydiacetate. G.C. analysis of the reaction mixture after a 6-hour reaction time showed it to contain 16.7% acetic anhydride.

COMPARATIVE EXAMPLE D

Again, Example I was repeated except that 0.04 mol per liter of zirconium was used in the form of zirconium hydride. G.C. analysis of the reaction mixture after a 4-hour reaction time showed it to contain 25.1% acetic anhydride.

COMPARATIVE EXAMPLE E

Repeating Comparative Example D but using 0.04 mol per liter of zirconium in the form of zirconium tetrachloride produced a reaction mixture after a 6-hour reaction time which G.C. analysis showed to contain 9.7% acetic anhydride.

COMPARATIVE EXAMPLE F

In this Example, 0.04 mol per liter of zirconium acetylacetonate was substituted for the zirconium compound of Comparative Example D but the reaction was otherwise the same. G.C. analysis of the reaction mixture after a 6-hour reaction time showed it to contain 4.1% acetic anhydride.

COMPARATIVE EXAMPLE G

In two experiments, Example I was again repeated except that triphenyl stibine and tri-n-butyl stibine in mol per liter quantities were substituted for the tri-phenyl arsine which was used in Example A. G.C. analysis of the reaction mixtures each after a 4-hour reaction time showed, in the case of tri-n-butyl stibine 0.4% acetic anhydride was produced and in the case of triphenyl stibine only 0.2% acetic anhydride.

COMPARATIVE EXAMPLE H

Example I was repeated a further time except that 0.04 mol per liter of titanium in powder form was used instead of zirconium. G.C. analysis of the reaction mixture after a 6-hour reaction time showed it to contain 27.2% acetic anhydride.

COMPARATIVE EXAMPLE I

Again repeating Example I, except that 0.04 mol per liter of niobium in powder form was used instead of zirconium. G.C. analysis of the reaction mixture after a 4-hour reaction time showed it to contain 9.1% acetic anhydride.

COMPARATIVE EXAMPLE J

Repeating Example I again but using 0.04 mol per liter of tantalum in powder form instead of zirconium produced a reaction mixture after a 6-hour reaction time which G.C. analysis showed to contain 15.4% acetic anhydride.

What is claimed is:

1. A process for the preparation of acetic anhydride which comprises reacting carbon monoxide, a halide which is an iodide or bromide and a compound selected from the group consisting of methyl acetate and dimethyl ether under substantially anhydrous conditions in the presence of 1 to 75 weight percent acetic acid, in the presence of a Group VIII noble metal catalyst and in the presence of a multiple promoter comprising metallic zirconium, and an organo-phosphorus compound or an organo nitrogen compound wherein the phosphorus and nitrogen are trivalent, or an arsine of the formula:

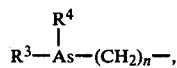

wherein R and $R^1$ are monocyclic aryl groups or alkyl groups and $R^2$ is the radical $$R^3—\underset{\underset{R^4}{|}}{As}—(CH_2)_n—,$$

a monocyclic aryl group or an alkyl group, and wherein $R^3$ and $R^4$ are each a monocyclic aryl group or an alkyl group, n being zero or a digit from 1–20.

2. A process as defined in claim 1, wherein the Group VIII noble metal is rhodium.

3. A process as defined in claim 1, wherein the halide is a hydrocarbyl halide.

4. A process as defined in claim 1, wherein the organic promoter component is an arsine.

5. A process as defined in claim 4, wherein the arsine is selected from the group consisting of triphenylarsine, methyl diphenylarsine and dimethylphenylarsine.

6. A process as defined in claim 1, wherein the amount of acetic acid is 10 to 30 weight percent.

7. A process as defined in claim 1, wherein the amount of acetic acid is 10 to 30 weight percent, the Group VIII noble metal is rhodium and the halide is a hydrocarbyl iodide.

* * * * *